(12) United States Patent
Wang

(10) Patent No.: US 12,569,121 B2
(45) Date of Patent: Mar. 10, 2026

(54) SLEEVE ASSEMBLY AND ENDOSCOPE DEVICE

(71) Applicant: Point Robotics Medtech Inc., Hsinchu County (TW)

(72) Inventor: Ren-Jeng Wang, Hsinchu County (TW)

(73) Assignee: Point Robotics Medtech Inc., Hsinchu County (TW)

( * ) Notice: Subject to any disclaimer, the term of this patent is extended or adjusted under 35 U.S.C. 154(b) by 164 days.

(21) Appl. No.: 18/739,268

(22) Filed: Jun. 10, 2024

(65) Prior Publication Data

US 2025/0241517 A1 Jul. 31, 2025

(30) Foreign Application Priority Data

Jan. 29, 2024 (TW) ................................. 113103280

(51) Int. Cl.
A61B 1/00 (2006.01)
A61B 1/018 (2006.01)
A61B 1/05 (2006.01)

(52) U.S. Cl.
CPC ...... A61B 1/00135 (2013.01); A61B 1/00128 (2013.01); A61B 1/018 (2013.01); A61B 1/053 (2013.01)

(58) Field of Classification Search
CPC ............ A61B 1/00128; A61B 1/00135; A61B 1/00154; A61B 1/018; A61B 1/053;
(Continued)

(56) References Cited

U.S. PATENT DOCUMENTS

2002/0022764 A1* 2/2002 Smith ................ A61B 17/3421
600/102
2021/0315660 A1* 10/2021 Williams ......... A61B 17/00234
(Continued)

FOREIGN PATENT DOCUMENTS

CN 203059795 U 7/2013
CN 104083140 A 10/2014
(Continued)

OTHER PUBLICATIONS

Search Report issued on Nov. 13, 2024 for EP application No. 24181632.1.

*Primary Examiner* — Md N Haque
(74) *Attorney, Agent, or Firm* — Li & Cai Intellectual Property Office

(57) ABSTRACT

A sleeve assembly and an endoscope device are provided. The endoscope device includes the sleeve assembly and a lens assembly. The sleeve assembly includes an outer sleeve and an inner sleeve. The outer sleeve has a first opening and a second opening that communicate with each other. The outer sleeve is configured to define a central axis, and the central axis passes through the first opening and the second opening. The inner sleeve is detachably disposed on the outer sleeve. The inner sleeve includes an annular component. The annular component is disposed outside the outer sleeve and surrounds the outer sleeve. The inner sleeve is disposed inside the outer sleeve and closely attached to an inner wall of the outer sleeve. The inner sleeve is configured to be operated to rotate relative to the central axis. The lens assembly is disposed in the inner sleeve.

17 Claims, 7 Drawing Sheets

(58) Field of Classification Search
CPC .............. A61B 1/3135; A61B 17/3421; A61B
2017/3445; A61B 2090/3614; A61B
90/361; A61B 90/57
See application file for complete search history.

(56) References Cited

U.S. PATENT DOCUMENTS

| | | | | |
|---|---|---|---|---|
| 2023/0172436 A1* | 6/2023 | Chu | ..................... | A61B 1/2676 |
| | | | | 600/104 |
| 2023/0233069 A1* | 7/2023 | Un | ...................... | A61B 1/0676 |
| | | | | 600/109 |
| 2023/0355337 A1* | 11/2023 | Huang | ................... | A61B 34/71 |

FOREIGN PATENT DOCUMENTS

| | | |
|---|---|---|
| CN | 209220356 U | 8/2019 |
| CN | 113081089 A | 7/2021 |

* cited by examiner

SLEEVE ASSEMBLY AND ENDOSCOPE DEVICE

CROSS-REFERENCE TO RELATED PATENT APPLICATION

This application claims the benefit of priority to Taiwan Patent Application No. 113103280, filed on Jan. 29, 2024. The entire content of the above identified application is incorporated herein by reference.

Some references, which may include patents, patent applications and various publications, may be cited and discussed in the description of the present disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a sleeve assembly and an endoscope device, and more particularly to a sleeve assembly and an endoscope device capable of reducing interference between instruments and facilitating adjustment of viewing angles.

BACKGROUND OF THE DISCLOSURE

Generally speaking, many surgical procedures can be implemented only with the assistance of endoscopic equipment. However, conventional endoscopic equipment still has much room for improvement. For instance, the inner space of a sleeve in the endoscopic equipment is limited, thereby causing potential interference between surgical tools and endoscopes inserted into the sleeve. Furthermore, the view field seen by a physician through inserting the endoscope into the sleeve is limited, it is impossible to fully observe the area to be treated, and blind spots are easily formed. The situations mentioned above may increase the risk during treatment.

Therefore, how to overcome the above-mentioned problems through improvements in structural design has become one of the important issues to be solved in the related art.

SUMMARY OF THE DISCLOSURE

The present disclosure introduces a sleeve assembly and an endoscope device to address the aforementioned deficiencies in existing endoscopic equipment.

In order to solve the above-mentioned problems, one of the technical aspects adopted by the present disclosure is to provide a sleeve assembly, which includes an outer sleeve and an inner sleeve. The outer sleeve has a first opening and a second opening that communicate with each other, and is configured to define a central axis that passes through the first opening and the second opening. The inner sleeve is detachably disposed on the outer sleeve. The inner sleeve includes an annular component disposed outside the outer sleeve and surrounding the outer sleeve. The inner sleeve is disposed inside the outer sleeve and closely attached to an inner wall of the outer sleeve. The inner sleeve is configured to rotate relative to the central axis.

In order to solve the above-mentioned problems, another one of the technical aspects adopted by the present disclosure is to provide an endoscope device that includes a sleeve assembly and a lens assembly. The sleeve assembly includes an outer sleeve and an inner sleeve. The outer sleeve has a first opening and a second opening that communicate with each other. The outer sleeve is configured to define a central axis that passes through the first opening and the second opening. The inner sleeve is detachably disposed on the outer sleeve. The inner sleeve includes an annular component, and the annular component is disposed outside the outer sleeve and surrounds the outer sleeve. The inner sleeve is disposed inside the outer sleeve and closely attached to an inner wall of the outer sleeve. The inner sleeve is configured to be operated to rotate relative the central axis. The lens assembly is disposed in the inner sleeve.

Therefore, in the sleeve assembly and the endoscope device provided by the present disclosure, the inner sleeve is disposed on a sidewall of the outer sleeve and surrounds the outer sleeve, such that the inner sleeve is closely attached to the inner wall of the outer sleeve. In this way, when the lens assembly is disposed in the inner sleeve, the lens assembly remains close to the inner wall of the outer sleeve, thereby not occupying much of the internal space within the outer sleeve, and preventing surgical instruments from interfering with each other. Moreover, since the annular component of the inner sleeve is configured to surround the outer sleeve, an endoscope is allowed to move freely along the inner wall of the outer sleeve, which enables a user (i.e., a doctor) to view different areas of the surgical site. Therefore, the problem that blind spots occur when using conventional endoscopes can be resolved.

These and other aspects of the present disclosure will become apparent from the detailed description of the embodiment, which should be read in conjunction with the accompanying drawings. The drawings and their descriptions, however, may be modified within the scope of the novel concepts of the present disclosure without straying from its fundamental principles.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Embodiment

Figure 1:
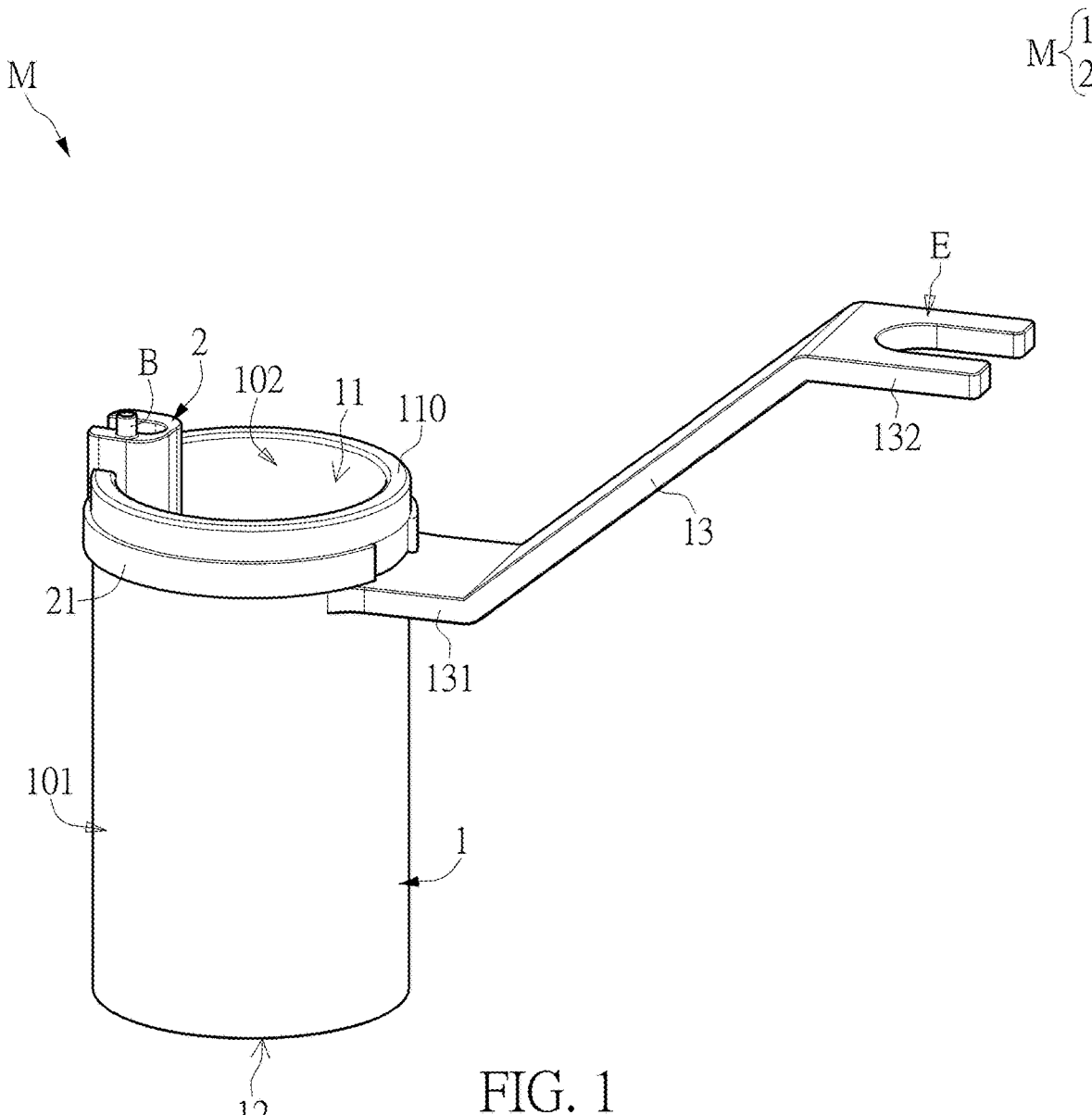
FIG. 1 is a schematic perspective view of a sleeve assembly according to the present disclosure.
Figure 2:
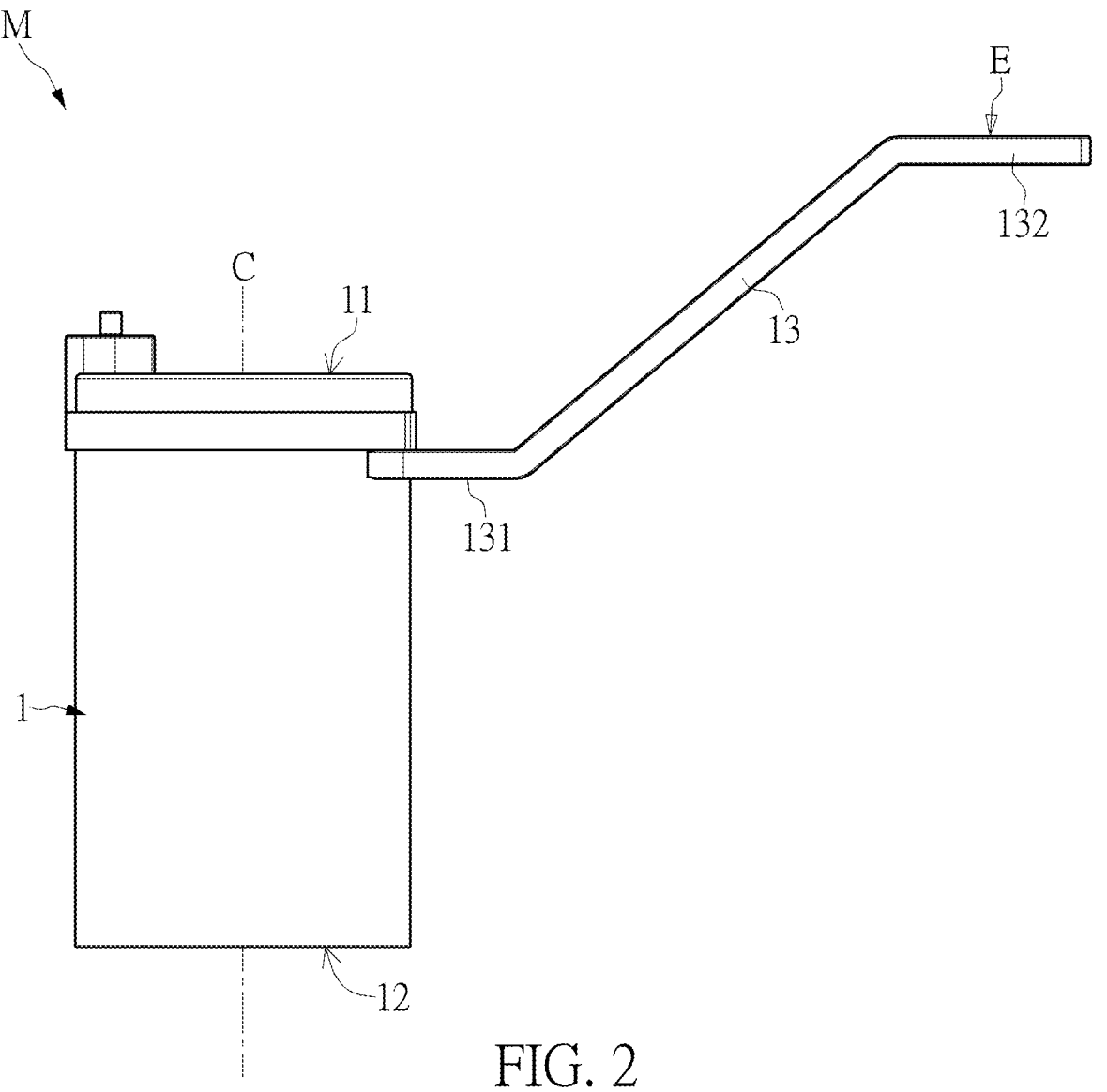
FIG. 2 is a schematic side view of the sleeve assembly according to the present disclosure.

Reference is made to FIGS. 1 and 2. FIG. 1 is a schematic perspective view of a sleeve assembly according to the present disclosure, and FIG. 2 is a schematic side view of the sleeve assembly according to the present disclosure. The present disclosure introduces a sleeve assembly M, which includes an outer sleeve 1 and an inner sleeve 2. The inner sleeve 2 is detachably mounted on the outer sleeve 1.

The outer sleeve 1 is a cylindrical hollow sleeve that has a first opening 11 and a second opening 12, and the first opening 11 and the second opening 12 communicate with each other. Along a direction extending from the first opening 11 toward the second opening 12, the outer sleeve 1 can define a central axis C that passes through the first opening 11 and the second opening 12. Additionally, the outer sleeve 1 further includes a connecting rod 13, and the shape of the connecting rod 13 is not limited by the present disclosure. The connecting rod 13 has a first end 131 and a second end 132. The first end 131 is connected to an outer wall 101 of the outer sleeve 1, and the second end 132 has an end surface E. The central axis C is perpendicular to the end surface E.

As depicted in FIG. 1, the second end 132 of the outer sleeve 1 includes a notch, so the outer sleeve 1 can be fixed to an external device through the notch by various connection manners, such as snapping, tenoning or bolting, which ensures that the outer sleeve 1 is oriented perpendicular to the end surface E.

Figure 3:
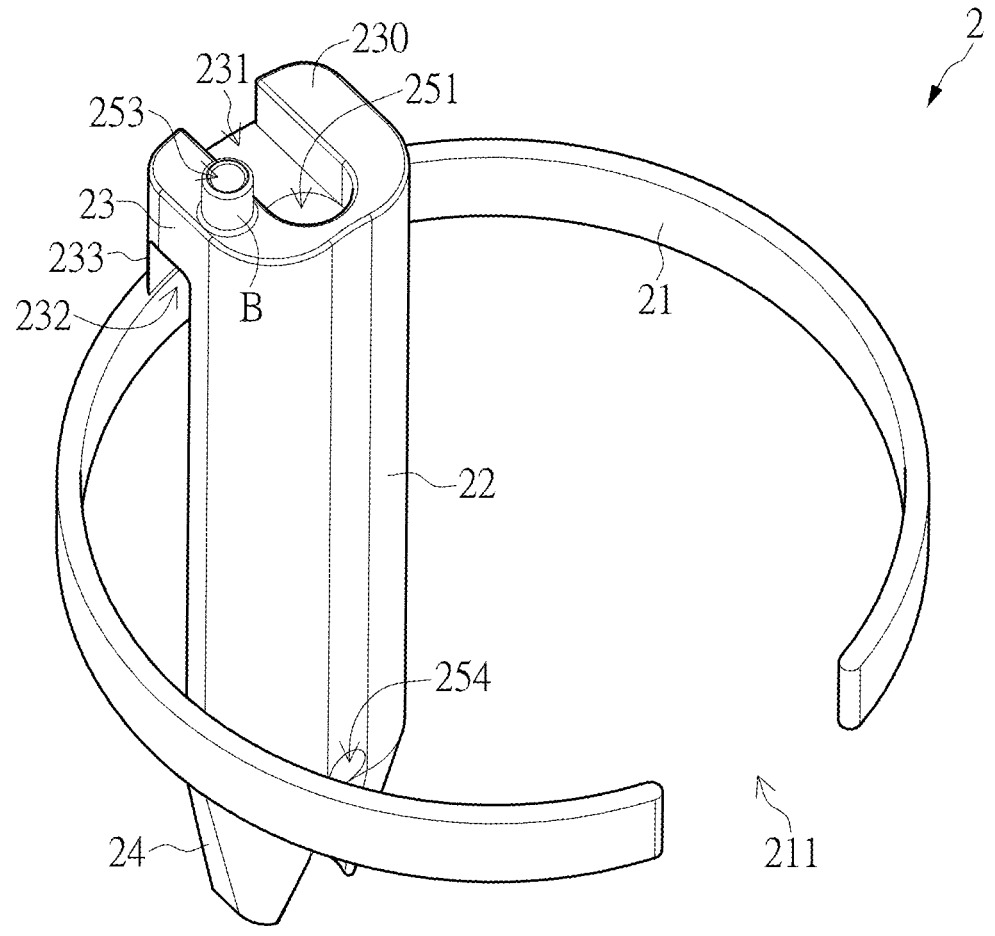
FIG. 3 is a schematic perspective view of an inner sleeve of the sleeve assembly according to the present disclosure.
Figure 4:
FIG. 4 is another schematic perspective view of the inner sleeve of the sleeve assembly according to the present disclosure.
Figure 4:
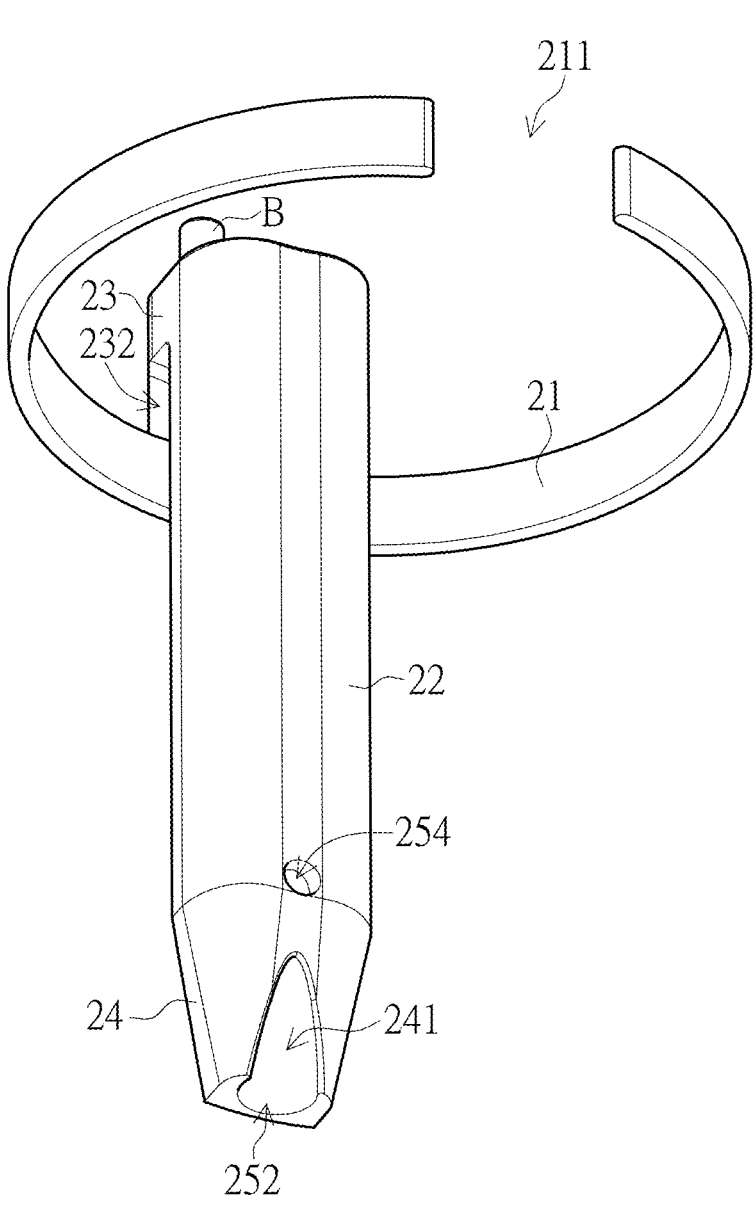
Figure 5:
FIG. 5 is yet another schematic perspective view of the inner sleeve of the sleeve assembly according to the present disclosure.
Figure 5:
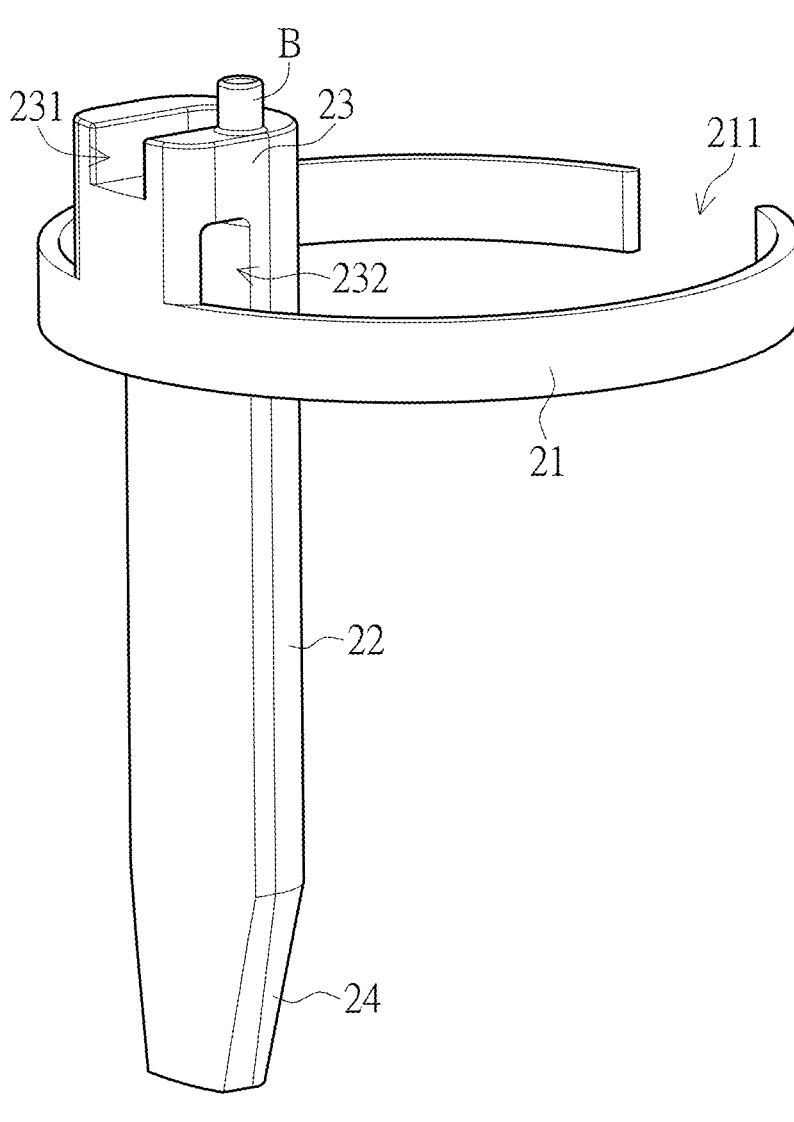

Reference is made to FIGS. 3 to 5. FIG. 3 is a schematic perspective view of an inner sleeve of the sleeve assembly according to the present disclosure, FIG. 4 is another schematic perspective view of the inner sleeve of the sleeve assembly according to the present disclosure, and FIG. 5 is yet another schematic perspective view of the inner sleeve of the sleeve assembly according to the present disclosure. The inner sleeve 2 includes an annular component 21, a body 22, a first end portion 23, and a second end portion 24. The first end portion 23 and the second end portion 24 are connected to opposite ends of the body 22, respectively. A top end surface 230 of the first end portion 23 is designed to form a first clamping slot 231, while the first end portion 23 also includes a connecting portion 233 situated on a side opposite to the top end surface 230. Additionally, the first end portion 23 extends from one side of the body 22, thereby allowing the first end portion 23, the connecting portion 233, and the body 22 to collectively form a second clamping slot 232.

Furthermore, the annular component 21 features an opening 211, and the connecting portion 233 of the first end portion 23 is connected to the annular component 21 at a side opposite to the opening 211. As illustrated in FIGS. 1 and 3, because the annular component 21 has the structure of the opening 211, the annular component 21 is essentially an annular cantilever. When the inner sleeve 2 is assembled to the outer sleeve 1, the annular component 21 of the inner sleeve 2 is positioned outside the outer sleeve 1, and surrounds the outer wall 101 of the outer sleeve 1. Additionally, the second clamping slot 232 clamps onto an edge 110 of the first opening 11 of the outer sleeve 1, so as to ensure that the inner sleeve 2 is closely affixed to an inner wall 102 of the outer sleeve 1. Through the design of the annular component 21 and the second clamping slot 232, the inner sleeve 2 can be stably mounted on the outer sleeve 1, closely affixed to the inner wall 102 of the outer sleeve 1, and then move freely along the inner wall 102. In this way, the inner sleeve 2 is capable of rotating around the central axis C of the outer sleeve 1.

Further reference is made to FIGS. 3 to 5. The inner sleeve 2 has a first passage port 251 and a second passage port 252, which communicate with each other. The first passage port 251 is located within the first clamping slot 231, while the second passage port 252 is located in the second end portion 24. As illustrated in FIG. 4, an outline of the second end portion 24 is tapered along a direction from the body 22 toward the second passage port 252. Additionally, the inner sleeve 2 includes a third passage port 253 and a fourth passage port 254, which also communicate with each other. The third passage port 253 is situated on the top end surface 230 of the first end portion 23. Specifically, a pillar B (as referenced in FIG. 1) can be formed on the top end surface 230 of the first end portion 23, and the third passage port 253 forms an opening on the pillar B. The fourth passage port 254 is located on the side of the body 22 and adjacent to the second end portion 24. Furthermore, as depicted in FIG. 4, the fourth passage port 254 and the second clamping slot 232 are respectively positioned on opposite sides of the body 22.

Figure 6:
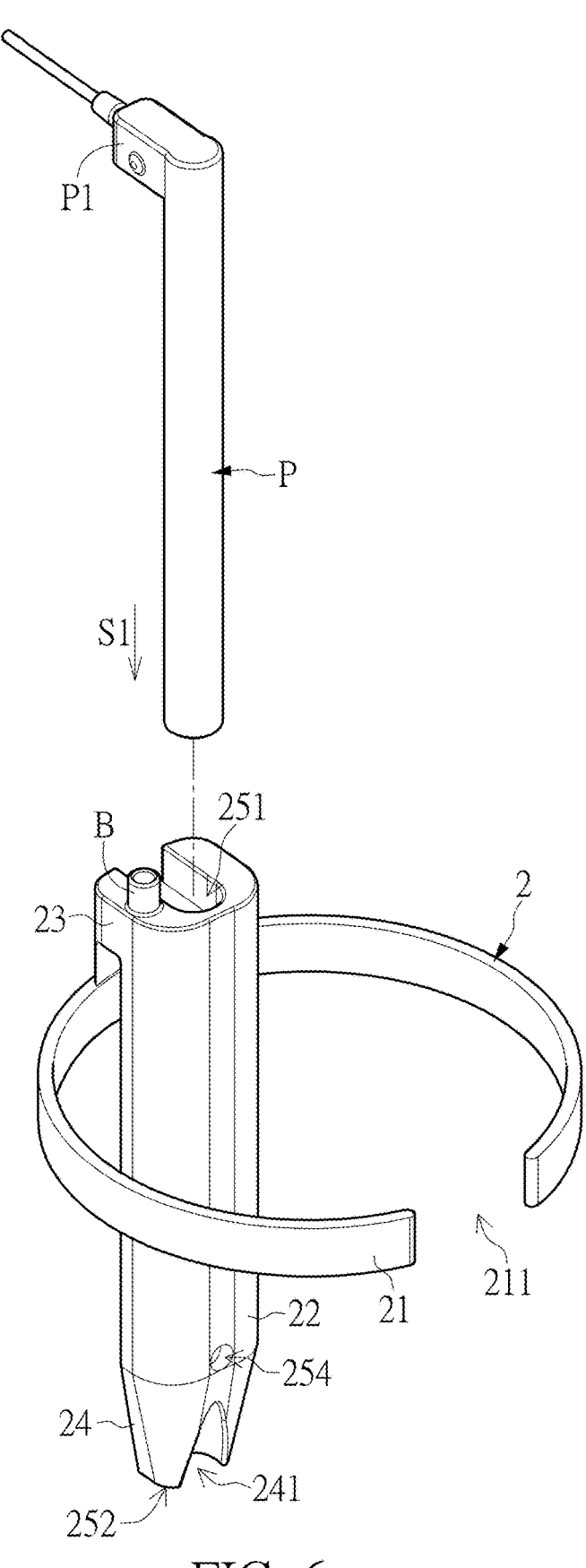
FIG. 6 is a schematic view showing assembly of an endoscope and the inner sleeve according to the present disclosure.
Figure 7:
FIG. 7 is a schematic perspective view of an endoscope device according to the present disclosure.

Reference is made to FIGS. 6 and 7. FIG. 6 is a schematic view showing assembly of an endoscope and the inner sleeve according to the present disclosure, and FIG. 7 is a schematic perspective view of an endoscope device according to the present disclosure. The present disclosure introduces an endoscope device D, which may include the aforementioned sleeve assembly M and a lens assembly P. The lens assembly P can be inserted into the inner sleeve 2. In more detail, the lens assembly P is an endoscope which can be inserted into the first passage port 251 along a direction S1, and can exit from the second passage port 252. Additionally, the endoscope device D may be externally connected to a flushing pipeline (not shown in the figures), in which the flushing pipeline can be inserted into the third passage port 253 (as indicated in FIG. 3) and allow water to flow out from the fourth passage port 254 (as marked in FIG. 6).

When a user (i.e., a doctor) operates the endoscope device D of the present disclosure for a minimally invasive surgery, the sleeve assembly M is inserted into the body of a patient through a surface incision. Subsequently, the lens assembly P is extended into the inner sleeve 2, while surgical tools may be inserted into the outer sleeve 1 to reach a to-be-operated site of the patient. The lens assembly P can be electrically connected to an external microscope or a display screen (not depicted in the figures). Therefore, the doctor can use the microscope or the display screen to see actual situation at the surgical site captured by the lens assembly P while manipulating the surgical tools.

As illustrated in FIGS. 3 and 6, a head portion P1 of the lens assembly P can be lodged within the first clamping slot 231. In this way, the lens assembly P remains secured in the inner sleeve 2 and does not sway as the inner sleeve 2 moves along the inner wall 102 of the outer sleeve 1, and the image viewed by the user is prevented from being affected. Since the inner sleeve 2 closely leans on the inner wall 102 of the outer sleeve 1 and rotates around the central axis C of the outer sleeve 1, the lens assembly P does not take up excessive space within the outer sleeve 1. Hence, when the doctor is to do surgery, there is enough space within the outer sleeve 1 for the doctor to operate surgical tools, and the surgical tools will not interfere with the lens assembly P. Moreover, as the inner sleeve 2 can slide along the inner wall 102 of the outer sleeve 1, the user can conveniently adjust the position of the lens assembly P to alter viewing angles and observe different areas, thereby avoiding generation of blind spots in the view field.

Additionally, during surgical procedures, sometimes it is necessary to remove a few parts of the body tissue. For instance, in a minimally invasive spinal decompression surgery, a drill bit may be used to drill into the vertebra or remove bone spurs from the intervertebral disc, such that some bone debris is generated. These surgical byproducts can accumulate at the surgical site and potentially obstruct the lens of the lens assembly P. In such cases, the flushing pipeline can be utilized to deliver water and cleanse the surgical site.

Further reference is made to FIGS. 6 and 7. The second end portion 24 further has an incision 241 which is connected to the second passage port 252 and located adjacent to the fourth passage port 254. An outline of the incision 241 gradually increases along the direction from the body 22 toward the second passage port 252. By the design of the incision 241, more of the end, extending into the second end portion 24, of the lens assembly P can be exposed. Therefore, water from the flushing pipeline exits from the fourth passage port 254 and can flow downward along the incision 241 to further clean the lens of the lens assembly P.

Furthermore, in one embodiment of the present disclosure, both the inner sleeve 2 and the outer sleeve 1 are made of transparent or translucent material, thereby allowing light to penetrate through and illuminate the surgical site. In other words, the brightness of the image viewed by the user through the lens assembly P can be significantly enhanced.

Additionally, as depicted in FIG. 7, the endoscope device D of the present disclosure may further include a marking module 3 and at least one marking element 4. The marking module 3 can be mounted on the connecting rod 13 of the outer sleeve 1, while the at least one marking element 4 is placed on the inner sleeve 2. The marking module 3 may be formed by multiple infrared reflective balls. Similarly, the at least one marking element 4 can also be an infrared reflective ball. By utilizing the infrared positioning technology, the marking module 3 and the at least one marking element 4 can be taken as a reference for establishing a spatial coordinate system. Consequently, when the inner sleeve 2 and the lens assembly P mounted thereon rotate relative to the outer sleeve 1, a rotation angle of the inner sleeve 2 and the lens assembly P relative to the outer sleeve 1 can be determined through the configuration of the marking module 3 and the at least one marking element 4. In this way, the orientation of an endoscopic image displayed on the screen can be corrected.

Beneficial Effects of the Embodiment

In conclusion, in the sleeve assembly M and the endoscope device D provided by the present disclosure, the annular component 21 and the second clamping slot 232 of the inner sleeve 2 are designed such that the inner sleeve 2 can be positioned inside the outer sleeve 1 and closely lean against the inner wall 102. When the lens assembly P (i.e., the endoscope) is mounted on the inner sleeve 2, the lens assembly P will also closely lean against the inner wall 102 of the outer sleeve 1, thereby avoiding much of internal space occupied by the lens assembly P and preventing surgical instruments from interfering with each other. Additionally, since the annular component 21 clamps and surrounds the outer sleeve 1, and since the second clamping slot 232 is clamped onto the edge 110 of the first opening 11, the lens assembly P can move freely along the inner wall 102 of the outer sleeve 1. This design allows the user (i.e., the doctor) to easily adjust the position of the lens assembly P and alter the viewing angle for viewing different areas, so as to resolve the problem of image blind spots of existing endoscopes.

Moreover, the endoscope device D can be externally connected to the flushing pipeline (not depicted in the figures). This flushing pipeline can be inserted into the third passage port 253, and allow water to be expelled from the fourth passage port 254, so as to cleanse residues at the surgical site. Additionally, through the design of the incision 241 on the second end portion 24 of the inner sleeve 2, the water flowing from the fourth passage port 254 is directed downward along the incision 241, so as to further clean the lens of the lens assembly P.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A sleeve assembly, comprising:
    an outer sleeve having a first opening and a second opening that communicate with each other, wherein the outer sleeve is configured to define a central axis that passes through the first opening and the second opening; and
    an inner sleeve detachably disposed on the outer sleeve, wherein the inner sleeve includes an annular component disposed outside the outer sleeve and surrounding the outer sleeve, and the inner sleeve is disposed inside the outer sleeve and closely attached to an inner wall of the outer sleeve;
    wherein the inner sleeve is configured to rotate relative to the central axis, the inner sleeve includes a body, a first end portion, and a second end portion, the first end portion and the second end portion are respectively connected to two ends of the body, a first clamping slot is formed on a top end surface of the first end portion, and a second clamping slot is formed on a side opposite to the top end surface of the first end portion;
    wherein, when the inner sleeve is disposed on the outer sleeve, the second clamping slot clamps on a first opening edge of the outer sleeve.

2. The sleeve assembly according to claim 1, wherein the outer sleeve includes a connecting rod, one end of the connecting rod is connected to an outer wall of the outer sleeve, and the other end of the connecting rod has an end surface that is perpendicular to the central axis.

3. The sleeve assembly according to claim 1, wherein the inner sleeve includes a first passage port and a second passage port, the first passage port is disposed in the first clamping slot, and the second passage port is disposed at the second end portion.

4. The sleeve assembly according to claim 3, wherein an outline of the second end portion is tapered along a direction from the body toward the second passage port, the second end portion includes an incision, and the incision is connected to the second passage port.

5. The sleeve assembly according to claim 4, wherein an outline of the incision gradually increases along the direction from the body toward the second passage port.

6. The sleeve assembly according to claim 4, wherein the inner sleeve further includes a third passage port and a fourth passage port, the third passage port is disposed on the top end surface of the first end portion, the fourth passage port is disposed on a side of the body, and the fourth passage port is adjacent to the incision.

7. The sleeve assembly according to claim 1, wherein the first end portion includes a connecting portion, the annular component further has an opening, and the connecting portion is connected to the annular component at a side opposite to the opening.

8. The sleeve assembly according to claim 1, wherein the inner sleeve and the outer sleeve are transparent or translucent.

9. An endoscope device, comprising:

a sleeve assembly, wherein the sleeve assembly includes:

an outer sleeve having a first opening and a second opening that communicate with each other, wherein the outer sleeve is configured to define a central axis, and the central axis passes through the first opening and the second opening; and an inner sleeve detachably disposed on the outer sleeve, wherein the inner sleeve includes an annular component, the annular component is disposed outside the outer sleeve and surrounds the outer sleeve, and the inner sleeve is disposed inside the outer sleeve and closely attached to an inner wall of the outer sleeve; wherein the inner sleeve is configured to be operated to rotate relative to the central axis, the inner sleeve includes a body, a first end portion, and a second end portion, the first end portion and the second end portion are respectively connected to two ends of the body, a first clamping slot is formed on a top end surface of the first end portion, and a second clamping slot is formed on a side opposite to the top end surface of the first end portion;

wherein, when the inner sleeve is disposed on the outer sleeve, the second clamping slot clamps on a first opening edge of the outer sleeve; and a lens assembly disposed in the inner sleeve.

10. The endoscope device according to claim 9, wherein the outer sleeve includes a connecting rod, one end of the connecting rod is connected to an outer wall of the outer sleeve, the other end of the connecting rod has an end surface, and the central axis is perpendicular to the end surface.

11. The endoscope device according to claim 9, wherein the inner sleeve includes a first passage port and a second passage port, the first passage port is disposed in the first clamping slot, and the second passage port is disposed at the second end portion; wherein the lens assembly is inserted through the first passage port and extends out from the second passage port, and a head portion of the lens assembly is clamped in the first clamping slot.

12. The endoscope device according to claim 11, wherein an outline of the second end portion is tapered along a direction from the body toward the second passage port, the second end portion has an incision, and the incision is connected to the second passage port.

13. The endoscope device according to claim 12, wherein an outline of the incision gradually increases along the direction from the body toward the second passage port.

14. The endoscope device according to claim 12, wherein the inner sleeve further includes a third passage port and a fourth passage port, the third passage port is disposed on the top end surface of the first end portion, the fourth passage port is disposed on a side of the body, and the fourth passage port is adjacent to the incision.

15. The endoscope device according to claim 14, further comprising a conveying pipe inserted into the third passage port and extending out from the fourth passage port.

16. The endoscope device according to claim 9, wherein the first end portion includes a connecting portion, the annular component further has an opening, and the connecting portion is connected to the annular component at a side opposite to the opening.

17. The endoscope device according to claim 9, wherein the inner sleeve and the outer sleeve are transparent or translucent.

* * * * *